(12) United States Patent
Wyszogrodzki

(10) Patent No.: US 6,248,120 B1
(45) Date of Patent: Jun. 19, 2001

(54) PUNCTURING DEVICE

(75) Inventor: Wojciech Wyszogrodzki, Daniszewska (PL)

(73) Assignee: P. Z. "HTL" Spolka Akcyjna, Warsaw (PL)

( * ) Notice: Subject to any disclaimer, the term of this patent is extended or adjusted under 35 U.S.C. 154(b) by 0 days.

(21) Appl. No.: 09/479,948

(22) Filed: Jan. 10, 2000

(51) Int. Cl.[7] ............................................. A61B 17/34
(52) U.S. Cl. ............................................. 606/182
(58) Field of Search ............................ 606/181, 182, 606/183, 184, 185, 188

(56) References Cited

U.S. PATENT DOCUMENTS

| | | | |
|---|---|---|---|
| 4,139,011 | 2/1979 | Benoit et al. ............... | 128/329 |
| 4,203,446 | * 5/1980 | Hofert et al. ............... | 606/182 |
| 4,527,561 | * 7/1985 | Burns ........................ | 606/181 |
| 5,356,420 | * 10/1994 | Czernecki et al. ........... | 606/182 |

\* cited by examiner

Primary Examiner—Kevin Truong
(74) Attorney, Agent, or Firm—Michael D. Bednarek; Shaw Pittman

(57) ABSTRACT

A puncturing device according to the invention comprises a sleeve (1), a push element (2) mounted at one end of the sleeve (1), a piston (5) having a puncturing tip (7) slidably mounted in the sleeve (1), a drive spring (9) positioned between the face end of the push element (2) and the piston (5) and a return spring (10) positioned inside the said sleeve (1) between its bottom (3) with an opening (4) for the puncturing tip (7) and the said piston (5) characterized in that the sleeve (1) has wings (11) directed inwardly and the projection (12) of the piston (5) rests on the said wings (11).

4 Claims, 3 Drawing Sheets

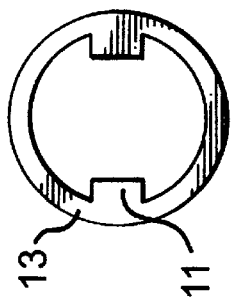
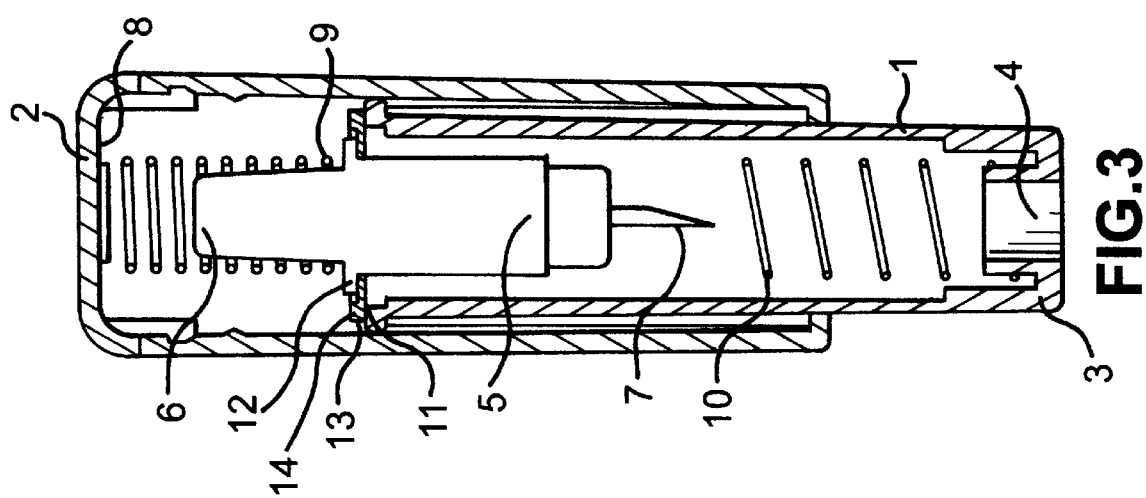

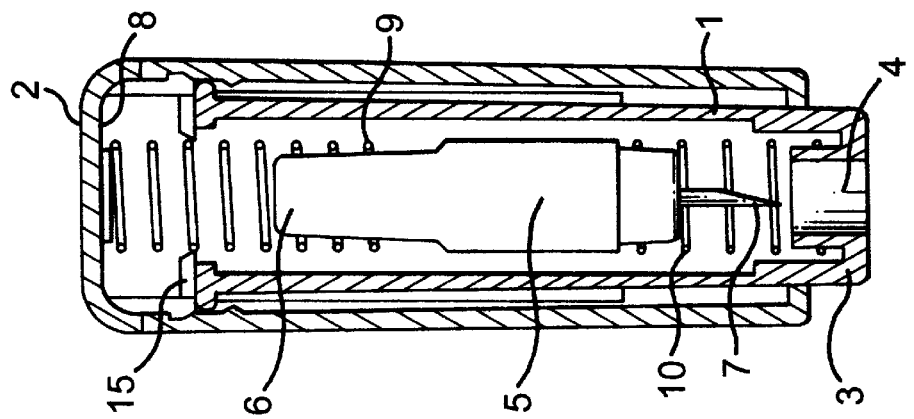
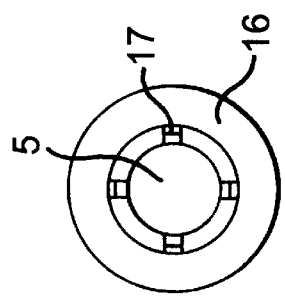
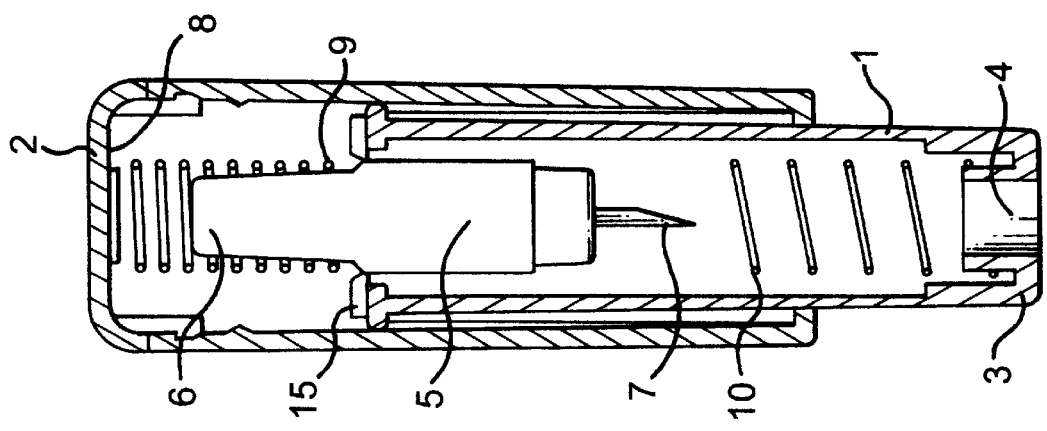

PUNCTURING DEVICE

The subject of the present invention is a puncturing device in particular for puncturing skin of a patient in order to take a blood sample for diagnostic purposes.

U.S. Pat. No. 4,139,011 discloses a device for puncturing skin of a patient comprising a housing in the form of a sleeve closed at one end and which, at the other end, narrows and has a small opening. Inside the housing there is a slidably mounted rod, which at one end terminates in a slider positioned inside the housing. At the other end there is a rod comprising an elastic arm terminating in a holding tooth, which rests on the edge of the opening in the housing. Between the rod and the bottom of the sleeve a spring is positioned and, at the other end of the slider, a puncturing insert is provided.

A device for puncturing comprising a sleeve and a push element for actuating the device positioned at one end of the sleeve is known from the U.S. Pat. No. 5,356,420. The opposite end of the sleeve is open. Inside the sleeve there is a slidably displacement piston, which at the end closer to the push element terminates in a head member, and which at the end closer to the open end of the sleeve terminates in a puncturing tip. Inside the sleeve, between the end face of the push element and the piston a driving spring is located, and between the piston and the open end of the sleeve there is a return spring positioned. The piston has, at the outer circumference thereof, wings which rest on an internal projection of the sleeve.

The puncturing device according to the invention comprises a sleeve, a push element positioned at one end of the sleeve, a piston and a puncturing tip slidably mounted in the sleeve, a drive spring positioned between the face end of the push element and the piston and a return spring positioned inside the sleeve between its bottom with an opening for the puncturing tip and the piston, and characterises in that a piston comprises a flange located at its outer rim resting against the top section of the sleeve and detaching from the piston when pressure is applied to the push element.

Preferably the flange comprises a ring and fasteners which bond the ring with the piston.

The advantage of the device according to the invention is that it provides a way of a fast and substantially painless piercing of skin, especially a skin on finger, ear or heel of a patient in order to take a blood sample for diagnostic purposes. The device, due to its structure, is expandable, because after the wings are broken off, it cannot be re-used.

Figure 1:
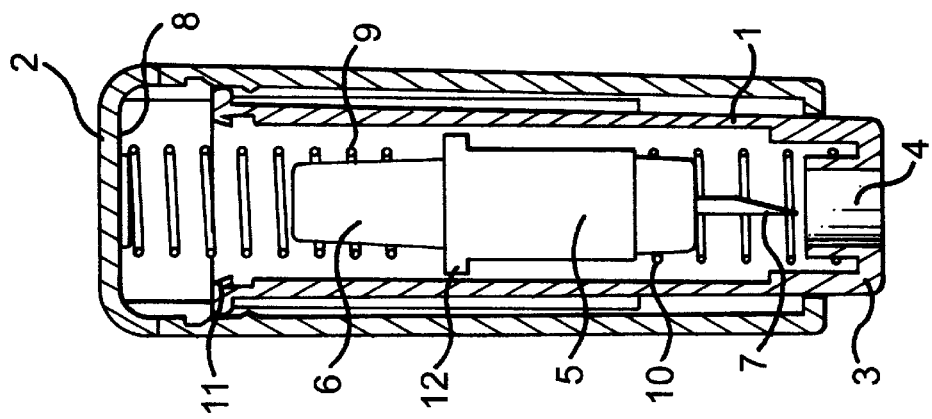
Figure 2:
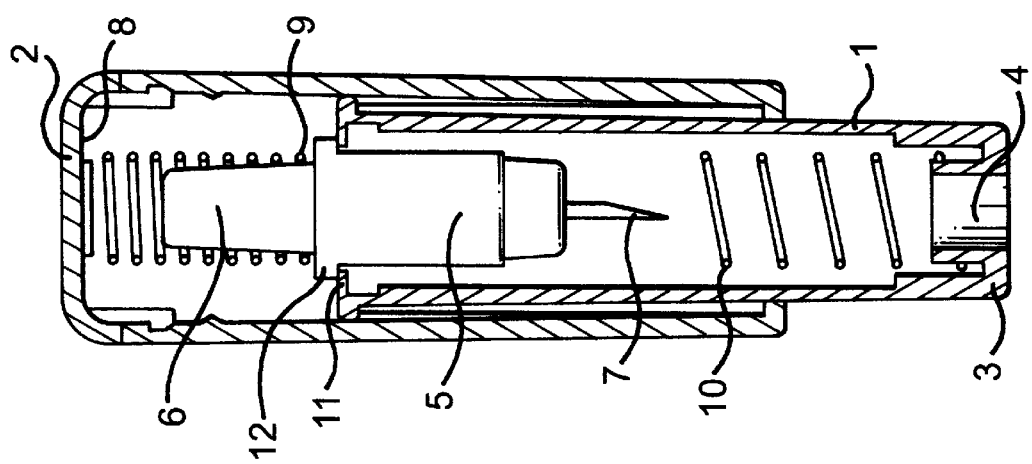

The subject matter of the invention will be understood more fully from the detailed description given below and from the accompanying drawings of various embodiments of the invention in which:

FIG. 1 presents a longitudinal section of the first embodiment of the device before use;

FIG. 2 presents a longitudinal section of the first embodiment after use;

FIG. 3—a longitudinal section of the second embodiment before use;

FIG. 4—a top view of the washer of the second embodiment of the device;

FIG. 5—a longitudinal section of the third embodiment before use;

FIG. 6—top view of the piston with the flange of th third embodiment of the device;

FIG. 7—a longitudinal section of the third embodiment of the device after use.

The puncturing device presented in the first embodiment as shown in FIGS. 1 and 2 comprises a sleeve 1 and a push element 2 monted at one end of the sleeve 1 and enclosing the sleeve at its substantial length. The other end of the sleeve 1 terminates in a bottom having an opening 4. A slidably mounted piston 5 is located in the sleeve 1, the piston, on the side of the push element 2 ends with a pusher 6, and on the side of the opening 4 of the bottom 3 of the sleeve 1 with a puncturing tip 7. A drive spring 9 is positioned inside the device between the face end 8 of the push element 2 and the piston 5. A return spring 10 is positioned inside the sleeve 1 between the piston 5 and the bottom 3 of the sleeve. The sleeve 1 in its upper section comprises wings 11 directed inwardly with a projection 12 situated at the side surface of the piston 5.

Below, we present the operation of the device according to the invention. Arrangement of the elements of the device before use is presented in FIG. 1. In result of the pressure applied by the device spring 9 the projection 12 of the sleeve 5 rests on the inward wings 11, which are positioned in the upper part of the sleeve 1. Thus, the piston 5 with the puncturing tip 7 is held in the first stable position. Pressing the push element 2 causes squeezing of the drive spring 9 to the point that the face end of the push element 2 rests on the pusher 6 of the piston 5. Applying further pressure to the push element 2 causes breaking off the wings 11 of the sleeve 1 by the projections 12 of the piston 5, the drive spring 9 actuates the piston 5 and the puncturing tip 7 extends through the opening 4 of the bottom of the sleeve 1 and punctures the skin. Next the return spring 10 withdraws the piston 5 with the puncturing tip 7 that takes the second stable position inside the sleeve 1. The position of the elements after use is illustrated in FIG. 2. Re-use of the device with broken off wings 11 is impossible.

Another embodiments of the puncturing device is shown at FIGS. 3 and 4. Reference numerals in respect of the main elements of the device are identical as in FIGS. 1 and 2. This embodiment is characterized by the fact that wings 11 together with the outer ring 13 form a washer 14 mounted at the upper part of the sleeve 1 and the wings 11 of the washer 14 rest at the projection 12 of the piston 5. Operation of the device is identical as presented in relation to FIGS. 1 and 2.

The third embodiment of the device according to the invention is illustrated by FIGS. 5 to 7. Reference numerals are identical as in FIGS. 1 to 4. In this embodiment the piston 5 at its outer rim comprises a flange 15 resting at the upper section of the sleeve 1. Flange 15 includes a ring 16 and fasteners 17, the fasteners 17 bond the ring 16 with the piston 5. The device of this embodiment operates in a similar way as described in relation to FIGS. 1 and 2 with a difference that due to the pressure applied at the push element 2 and further at the piston 5, the fasteners 17 are broken off causing the detachement of the piston 5 from the flange 15.

What is claimed is:

1. A puncturing device comprising a sleeve, a push element mounted at one end of the sleeve, a piston with a puncturing tip slidably mounted in the sleeve, a drive spring positioned between a face end of the push element and the piston and a return spring positioned inside the sleeve between another end of the sleeve and the piston, wherein the sleeve (1) has breakable wings (11) directed inwardly and the piston (5) has an external projection (12) which rests on said wings (11).

2. A puncturing device comprising a sleeve, a push element mounted at one end of the sleeve, a piston with a puncturing tip slidably mounted in the sleeve, a drive spring positioned between a face end of the push element and the piston and a return spring positioned inside the sleeve between another end of the sleeve and the piston, wherein a washer including breakable wings (11) rests on an outer ring positioned on the top of the sleeve (1), and wherein the piston (5) has an external projection (12) which rests on said wings (11).

3. A puncturing device comprising a sleeve, a push element mounted at one end of the sleeve, a piston with a puncturing tip slidably mounted in the sleeve, a drive spring positioned between a face end of the push element and the piston and the return spring positioned inside the sleeve between another end of the sleeve and the piston, wherein the piston (5) at its outer rim includes a flange (15) which, in a pre-operation state, rests on the top of the sleeve (1) and, in an operational state, detaches from the piston (5) when pressure is applied at the push element (2).

4. A puncturing device according to claim 3 wherein the flange (15) comprises a ring (16) which is in communication with the piston (5) by breakable fasteners (17).

* * * * *